United States Patent [19]

Rolf et al.

[11] Patent Number: 5,741,510
[45] Date of Patent: *Apr. 21, 1998

[54] ADHESIVE PATCH FOR APPLYING ANALGESIC MEDICATION TO THE SKIN

[75] Inventors: David Rolf, Minneapolis, Minn.; Elisabeth K. Sjoblom Urmann, Tomahawk, Wis.

[73] Assignee: Lectec Corporation, Minnetonka, Minn.

[*] Notice: The term of this patent shall not extend beyond the expiration date of Pat. No. 5,536,263.

[21] Appl. No.: 629,191

[22] Filed: Apr. 8, 1996

Related U.S. Application Data

[63] Continuation of Ser. No. 219,982, Mar. 30, 1994, Pat. No. 5,536,263.

[51] Int. Cl.$^6$ .................................................. A61F 13/02
[52] U.S. Cl. .................. 424/448; 424/449; 604/307
[58] Field of Search ................... 424/448, 449; 604/307

[56] References Cited

U.S. PATENT DOCUMENTS

| | | | |
|---|---|---|---|
| 2,137,169 | 11/1938 | Leveu | 167/84 |
| 3,249,109 | 5/1966 | Maeth et al. | 128/268 |
| 3,339,546 | 9/1967 | Chen | 128/156 |
| 3,428,043 | 2/1969 | Shepherd | 128/268 |
| 3,598,122 | 8/1971 | Zaffaroni | 128/268 |
| 3,612,053 | 10/1971 | Pratt | 128/283 |
| 3,640,741 | 2/1972 | Etes | 106/170 |
| 3,731,683 | 5/1973 | Zaffaroni | 128/268 |
| 3,742,951 | 7/1973 | Zaffaroni | 128/268 |
| 3,767,784 | 10/1973 | Gluck | 424/28 |
| 3,814,095 | 6/1974 | Lubens | 128/260 |
| 3,972,995 | 8/1976 | Tsak et al. | 424/28 |
| 3,998,215 | 12/1976 | Anderson et al. | 128/2.06 E |
| 4,002,221 | 1/1977 | Buchalter | 181/0.5 |
| 4,089,329 | 5/1978 | Courvillon, Jr. et al. | 128/2 T |
| 4,125,110 | 11/1978 | Hymes | 128/2.06 E |
| 4,253,460 | 3/1981 | Chen et al. | 128/283 |
| 4,274,420 | 6/1981 | Hymes | 128/641 |
| 4,299,231 | 11/1981 | Karmann et al. | 128/639 |
| 4,306,551 | 12/1981 | Hymes et al. | 128/156 |
| 4,307,717 | 12/1981 | Hymes et al. | 128/156 |
| 4,457,748 | 7/1984 | Lattin et al. | 604/20 |
| 4,474,570 | 10/1984 | Ariura et al. | 604/20 |
| 4,515,162 | 5/1985 | Yamamoto et al. | 128/640 |
| 4,585,652 | 4/1986 | Miller et al. | 424/83 |
| 4,593,053 | 6/1986 | Jevne et al. | 523/111 |
| 4,638,043 | 1/1987 | Szycher et al. | 528/75 |
| 4,675,009 | 6/1987 | Hymes et al. | 604/304 |
| 4,692,273 | 9/1987 | Lawrence | 252/518 |
| 4,694,835 | 9/1987 | Strand | 128/640 |
| 4,696,854 | 9/1987 | Ethier | 428/287 |

(List continued on next page.)

OTHER PUBLICATIONS

"External Analgesic Drug Products for Over-the-Counter Use; Tentative Firial Monograph" *Federal Register*, Tuesday, Feb. 8, 1983 (19 pp.).

*Primary Examiner*—D. Gabrielle Phelan
*Attorney, Agent, or Firm*—James V. Harmon

[57] ABSTRACT

A medication patch to be applied to the skin includes a self-supporting backing layer to give the patch the required integrity and strength by acting as a supporting framework for other components, and a flexible hydrophilic pressure-sensitive adhesive reservoir comprising a natural or synthetic polymer for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication-containing reservoir. The medication within the reservoir migrates over time from within the backing through the lower coating layer and passes through the skin to provide sustained release of the medication into the body of a patient.

14 Claims, 1 Drawing Sheet

U.S. PATENT DOCUMENTS

| | | | |
|---|---|---|---|
| 4,702,732 | 10/1987 | Powers et al. | 604/20 |
| 4,704,282 | 11/1987 | Campbell et al. | 424/449 |
| 4,717,378 | 1/1988 | Perrault et al. | 604/20 |
| 4,778,786 | 10/1988 | Reever et al. | 514/54 |
| 4,989,607 | 2/1991 | Keusch et al. | 128/640 |
| 5,002,792 | 3/1991 | Vegoe | 427/2 |
| 5,123,423 | 6/1992 | Schamberg | 128/798 |
| 5,142,817 | 9/1992 | Rolf | 47/24 |
| 5,205,297 | 4/1993 | Montecalvo et al. | 128/798 |
| 5,224,967 | 7/1993 | Rolf et al. | 47/58 |

U.S. Patent
Apr. 21, 1998
5,741,510
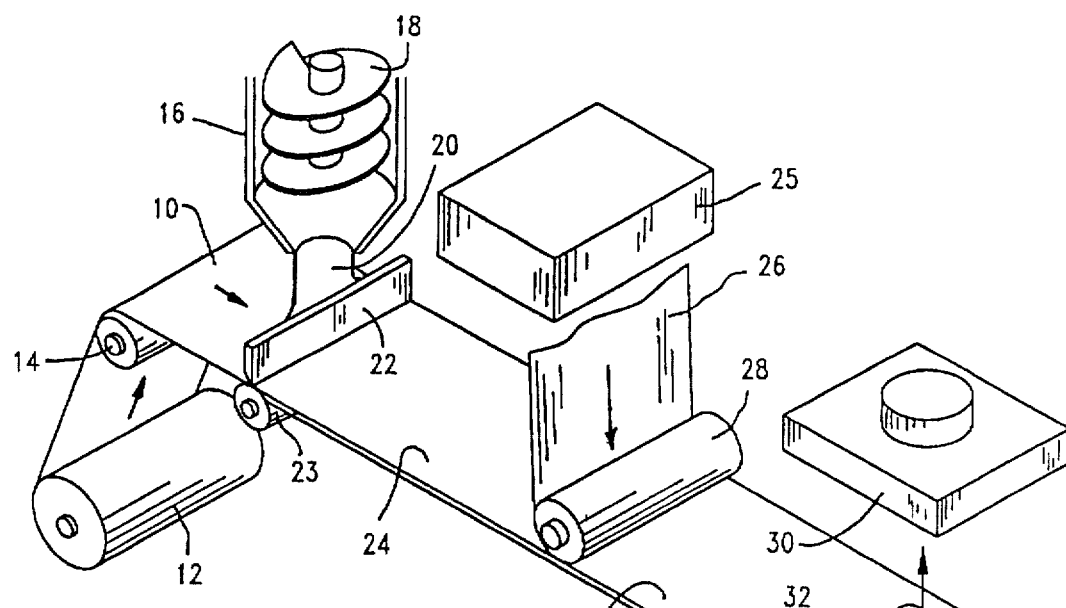
FIG. 1
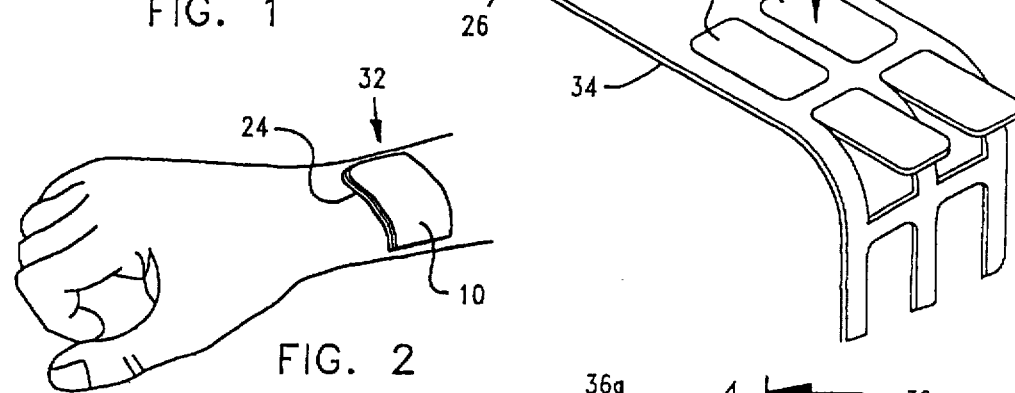
FIG. 2
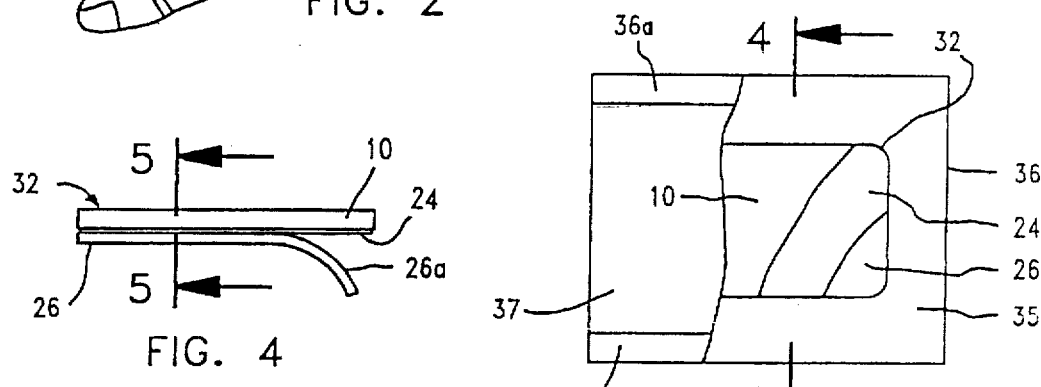
FIG. 4
FIG. 3
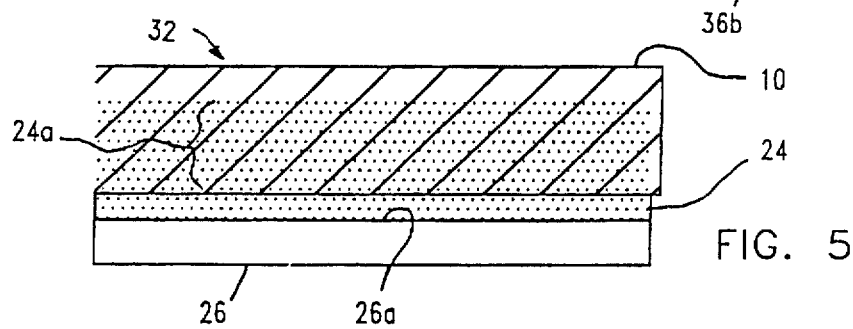
FIG. 5

5,741,510

ADHESIVE PATCH FOR APPLYING ANALGESIC MEDICATION TO THE SKIN

This application is a continuation of application Ser. No. 08/219,982 filed Mar. 30, 1994, now U.S. Pat. No. 5,536,263.

FIELD OF THE INVENTION

This invention relates to an improved adhesive patch for applying medication to the skin.

BACKGROUND OF THE INVENTION

Several kinds of patch devices have been used in the past for applying medication to the skin. For example, U.S. Pat. No. 4,675,009 describes a drug dispensing device for transdermal delivery of medication in which a natural or synthetic polysaccharide or synthetic polymer functions as a non-biodegradable adhesive reservoir. These patches, while very good, are so thick and cumbersome that users complain of their appearance and the discomfort associated with their use. Another deficiency is found in analgesic patch products that contain a robber sheet backing which occludes the skin, making moisture evaporation virtually impossible.

One important object of the present invention is to provide a non-occlusive analgesic patch, i.e., one which will enable moisture vapor on the surface of the skin to evaporate through the patch so as to prevent the undesired accumulation of moisture which, if it occurred, could cause the patch to fall off or even facilitate the growth of bacteria beneath the patch.

Another objective of the present invention is to provide a much lighter, more flexible and less obtrusive patch while still providing excellent sustained release properties during eight hours or more of use.

Another more specific object is to find a way to enable the backing of the adhesive tape itself to serve as a reservoir for the sustained release of a medication to be applied topically into the skin.

Still another more specific object is to unify a porous backing and a hydrophilic pressure-sensitive hydrocolloidal dispersion which serves as a reservoir for medication so as to provide sustained release of the medication while reducing the thickness and bulk of the patch and improving its flexibility.

A further more specific object of the present invention is to provide a more comfortable and less obtrusive topical analgesic patch for the temporary relief of pain including arthritis pain, backaches as well as muscular aches and strains.

Yet another object is to provide an improved method of combining the porous backing and the hydrocolloidal medication-containing pressure-sensitive adhesive reservoir during manufacture.

These and other more detailed and specific objects of the present invention will be better understood by reference to the following figures and detailed description which illustrate by way of example but a few of the various forms of the invention within the scope of the appended claims.

SUMMARY OF THE INVENTION

Briefly, the present invention provides a non-occlusive medication patch to be applied to the skin. It includes a porous self-supporting backing layer to give the patch the required integrity and strength by acting as a supporting framework for other components, and a flexible hydrophilic pressure-sensitive adhesive reservoir comprising a hydrocolloidal gel for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication-containing reservoir. In this way, the medication within the reservoir migrates over time from within the backing through the lower coating layer and passes through the skin to provide sustained release of the medication into the body of a patient.

The reservoir comprises a hydrocolloidal dispersion of a natural or synthetic gel-forming polymer, a hydrophilic adhesive, a hydrophilic humectant and a biomedically active medication, i.e., a medicament, dispersed throughout the reservoir including both the external portion and the internal portion that infiltrates the porous backing.

The invention provides a comfortable, highly flexible patch that is thinner than prior patches, conforms to the body contours, is better tolerated by patients, and is considered by patients to be more unobtrusive. The invention provides outstanding results as a non-occlusive analgesic patch that can be adhered to the skin to release an analgesic for the relief of pain including arthritis pain, backache as well as muscular aches and strains. In such an application, the analgesic comprises trolamine salicylate, menthol salicylate, menthol, camphor, eucalyptus oil or spearmint oil, or a combination thereof.

The invention will be better understood by reference to the following specification and accompanying drawings.

BRIEF DESCRIPTION OF THE DRAWINGS

FIG. 1 is a perspective diagrammatic view illustrating a preferred method of forming products in accordance with the invention;

FIG. 2 is a perspective view of the improved medication patch applied to the body;

FIG. 3 is a plan view showing the medication patch packaged within in a pouch used as a shipping package;

FIG. 4 is a cross-sectional view of the medication patch taken on line 4—4 of FIG. 3 with a portion of the liner sheet partially removed; and FIG. 5 is a greatly enlarged microscopic view of the medication patch and liner sheet taken on line 5—5 of FIG. 4.

DETAILED DESCRIPTION OF THE INVENTION

Refer now to FIG. 1 which illustrates diagrammatically the production of medication-applying patches in accordance with the invention. The backing sheet 10 is unwound continuously from a supply roll 12, passes upwardly in the figure over an idler roll 14 and then travels horizontally beneath a continuous processing mixer 16 where freshly prepared fluid hydrogel material at 20 is applied to the upper surface of the backing sheet 10.

The backing 10 is a porous self-supporting sheet of water insoluble polymeric material that provides strength and integrity for the adhesive patch as well as acting as a substrate for receiving and retaining a portion of the liquid hydrogel as will be described below.

One preferred backing sheet 10 is a lightweight, pliable strip composed, for example, from a nonwoven fabric which consists of polymeric fibers such as polyester, cotton or cellulose fibers bonded together with a sizing resin. The backing sheet 10 should be nonirritating to human skin. If desired, the backing sheet 10 can be coated on its back surface with a release coating such as a silicone release coating as described in U.S. Pat. No. 4,696,854 which is incorporated herein by reference. One suitable release coating is a 100% solids electron beam curable silicone such as Tego® Resin Acrylates/RC-Series RC 705 and RC 726 by Goldschmidt Chemical Corporation of Hopewell, Va. The preferred backing sheet 10 is a porous polymeric water insoluble nonwoven fibrous fabric. A suitable sizing material for bonding the fibers together is a latex resin.

The backing sheet 10 can comprise other stable, water insoluble flexible sheet materials. One preferred backing comprises a 5.5 mil. strip of nonwoven fabric formed from a mixture of cellulose fibers derived from wood pulp and polyester fibers. The fibers are assembled loosely into the backing to maintain porosity. A unifying or sizing resin is applied to hold the fibers together. The sizing resin can comprise a nonirritating resin applied as a latex emulsion. One example is Hycar® 26477, a resin produced by B.F. Goodrich Co. of Brecksville, Ohio. Another suitable backing sheet is a nonwoven fabric comprising a wetlay cellulose and polyester nonwoven fabric containing as a sizing an acrylic latex emulsion resin, e.g., product number N7601 by Dexter Corporation of Windsor Locks, Conn.

In another embodiment of the invention, the backing sheet 10 comprises a porous woven 5 mil. acetate polymer cloth sometimes known as "silk cloth." Another form of backing sheet 10 is an open-cell plastic foam strip of low density polyethylene or polyvinyl acetate resin. Other backing sheets that can be used include woven cotton cloth or other cloth formed from a synthetic polymer. Suitable synthetic cloths include nylon, polyester, polyacetate. When the backing sheet 10 is a woven cloth, no sizing resin is needed. The backing sheet 10 is pervious to air so that the patch is non-occlusive to the skin.

The porosity of the backing sheet 10 is important because it provides openings for receiving the hydrocolloidal medication-containing reservoir and it helps to assure that the patch is non-occlusive to the skin. The infusion of the pressure-sensitive hydrocolloidal medication-containing reservoir into the backing sheet 10 is accomplished by controlling manufacturing parameters so as to keep the hydrocolloid sufficiently fluid to penetrate the backing sheet 10 in spite of its tendency to thicken rapidly when applied. In order to prevent the consistency of the hydrogel from building too fast, i.e., becoming too viscous to properly penetrate the backing sheet 10, a continuous processing mixer 16 (FIG. 1) which includes rotating auger 18 is chilled to help remove heat produced during mixing and keep the hydrogel cool until applied to the backing 10. This can be accomplished by providing the processing mixer 16 with a cooling jacket through which a coolant such as a chilled mixture of water and ethylene glycol is passed during operation. The components of the hydrogel are continuously added to the mixer 16 during operation. While any suitable mixer 16 can be used, one suitable mixer is a five-inch continuous processing mixer manufactured by Teledyne Readco Company of York, Pa. The coolant passed through the processing mixer 16 can be maintained at about 0° C. The temperature of the fluid hydrogel 20 as it flows onto the exposed surface of the backing sheet 10 is important for controlling the infiltration of the coating into the backing sheet 10. The coolant will, under typical operating conditions, keep the extruded hydrogel 20 at a temperature of about 9° C. to 14° C. as it comes into contact with the backing 10. If deeper penetration is desired, the temperature of the hydrogel is lowered to about 9° C. for a typical hydrogel formulation. If less penetration is wanted, the temperature is raised closer to 15° C.

The hydrogel produced by the processing mixer 16, which is in a chilled fluid condition, is expelled at 20 onto the exposed upper surface of the backing sheet 10 adjacent to a knife blade 22 of a knife coater which is held in spaced relationship above a rotatable support roll 23. The distance between the knife 22 and the roll 23 is controlled in any suitable manner, as by means of adjustment screws (not shown) or, if desired, the desired gap or spacing between the knife 22 and roll 23 can be preset to accommodate the backing sheet 10 and the thickness of the hydrogel coating 24 that is being applied to the exposed surface of the backing sheet 10.

In accordance with the invention, the medication-containing hydrogel 20 is applied so as to penetrate a substantial portion of the backing sheet 10, e.g., typically between one-fourth to nine-tenths the thickness of the backing sheet 10. The penetration of the coating 24 into the backing 10 can be seen in FIG. 5. In this case the hydrogel coating 24 has penetrated about three-fourths of the way through the backing sheet 10 to provide an upper, i.e., internal layer 24a of hydrocolloidal material within the pores between the fibers making up the porous backing sheet 10. The hydrogel material thus includes two layers as seen in FIG. 5; the external coating layer 24 with an exposed pressure-sensitive surface 24b and the upper internal portion 24a which infiltrates and becomes solidified within the backing in the interstices between the fibers that make up the porous backing sheet 10.

In one product with very good characteristics the backing sheet 10 is 5.5 mils in thickness and the external part of the coating layer 24 is 8 mils in thickness to provide a combined thickness for the patch when applied to the body of 13.5 mils. The external hydrogel layer 24 is purposely maintained relatively thin. The hydrocolloidal adhesive reservoir infiltrates into the backing to a depth of about 2–5 mils to provide a total hydrocolloid layer, including both the internal and external portions, of about 10–13 mils. Because of its thickness, the medication-containing reservoir provides a very adequate supply of medication to assure sustained release of the medication over an extended period of time, e.g., six to eight hours or more. During use, the medication in the internal reservoir portion 24a stored within the backing sheet 10 migrates from within the backing sheet 10 through the external coating layer 24 and then passes through the skin to provide sustained release of the medication into the body of the patient.

After the hydrogel layer 24 is applied to the backing 10, the backing sheet continues moving toward the right as seen in FIG. 1 into close proximity with an oven or heater, in this case a radiant electric heater 25 which radiates heat onto the hydrogel coating layer 24, raising its temperature to about 140° F. and causing it to cure, i.e., to set up as a solid that is sufficiently stable to maintain its own shape and resist flow during storage or use. Once the heater 25 has warmed the hydrogel coating 24, it will be solidified and dimensionally stable. A liner sheet 26 such as polyethylene coated paper is then applied continuously by pressing it onto the exposed surface of the hydrogel layer 24 as the liner sheet 26 passes beneath a rotating roll 28. The assembled laminate 34 then moves further toward the right in the figure where a die press 30 stamps separate patches 32 from the sheet material.

The hydrogel 20, 24 comprises a hydrocolloidal dispersion of a hydrophilic natural or synthetic gel-forming polymer, a hydrophilic humectant, a biomedically active substance or medication, i.e., a medicament, and a hydrophilic adhesive substance such as an aqueous dispersion of an acrylic adhesive.

The polymer can comprise a natural gum such as gum karaya, gum acacia, locust bean gum, guar gum, or other polysaccharide as well as synthetically formulated polysaccharides, e.g., modified guar gum, maltodextrin, or celluloses such as carboxymethyl cellulose and carboxypropyl cellulose. The polymer can also comprise a synthetic polymer such as polyacrylamide and its cogeners or polyacrylic acid. Polyacrylamide is sold under the trademark Polytec 31x by Tecna Corp., Belleville, N.J.

The humectant can comprise a polyhydric alcohol such as glycerol, propylene glycol, ethylene glycol, or sorbitol.

The adhesive can comprise any suitable biocompatible hydrophilic adhesive such as a resin emulsion adhesive, e.g., an acrylate emulsion adhesive or a copolymer of vinyl acetate and dioctyl maleate. The most outstanding results have been achieved with an acrylic emulsion adhesive. Other hydrophilic adhesives that can be used include an acrylic ester copolymer and a vinyl acetate resin.

Any of a variety of topical medications can be used in accordance with the present invention. When the patch is used as an analgesic, these include trolamine salicylate, methyl salicylate, menthol, camphor, eucalyptus oil, spearmint oil, or a combination thereof. In other applications, the medication can include anti-pruritic agents or anti-inflammatory agent such as hydrocortisone, or anesthetic agents such as benzocaine or lidocaine. Also included are non-steroidal anti-inflammatory agents such as ibuprofen, especially the S-isomer of ibuprofen. Other medications include keratolytic agents such as salicylic acid, and rubefacient agents such as capsicum.

In FIG. 2 the finished patch 32 is seen applied to the surface of the body with the backing 10 exposed and the pressure-sensitive hydrogel layer 24 bonded to the skin.

In FIG. 3 is shown a package containing the finished patch 32 as it appears during shipment and storage. The package 36 comprises a pouch including lower and upper layers of paper 35, 37 or other suitable packaging material such as metal foil coated paper which is sealed to itself along its edges, e.g., at 36a, 36b to provide a sealed pouch containing the finished patch 32.

As shown in FIGS. 4 and 5, the finished patch 32 includes the porous backing 10, the hydrogel coating including the lower, i.e., external hydrogel coating layer 24 and the upper or internal portion 24a that permeates the backing 10. The upper surface 26a of the liner sheet 26 is a release surface for facilitating its removal. Before use, the liner sheet 26 is removed by pulling it off the patch as shown at the right in FIG. 4 to expose the pressure-sensitive surface of the layer 24 which is then applied to the skin as shown in FIG. 2.

During use, the upper or internal reservoir portion 24a that infiltrates the backing 10 and is solidified therein serves to store the medication within the backing 10 so that the medication migrates over time from its location at 24a within the backing 10 through the external coating layer 24 and then passes through the skin to provide sustained release of the medication into the body of the patient.

The porosity of the backing 10 combined with the water compatibility of the hydrocolloidal dispersion also makes the patch non-occlusive so that moisture from the body can evaporate through the patch into the atmosphere. The moisture vapor transmission rate (MVTR) of the skin alone under various conditions is typically from about 70 to about 149 g/m$^2$/24 hr while the medication applying patch of the present invention is about 612 to 1952 g/m$^2$/24 hr. This shows that the invention is non-occlusive because in a given period of time about 8 to 14 times more moisture vapor is transmitted through the patch of the present invention than through the skin. Prior medication-applying patches that employed a rubber backing allow virtually no moisture evaporation from the skin. By contrast, the non-occlusive patch of the present invention will not interfere with moisture evaporation from the skin. This is important because the evaporation of moisture from the skin helps the skin to act in its normal capacity as a barrier to externally applied compounds which, if absorbed in excessive mounts, can produce toxic reactions or skin irritation. The invention thus enables the barrier function of the stratum corneum to be maintained.

When used as an analgesic patch, the present invention provides outstanding results in relieving pain such as arthritis pain and backache pain, as well as muscular aches and strains. Because of the thinness of the patch, it is perceived as being more comfortable, more flexible, less obtrusive and is more acceptable to the patient. The backing 10 is rendered so translucent by infiltration of the hydrocolloidal gel that the patch is very inconspicuous on the skin. The entire thickness of the analgesic patch is about 13.5 mils.

The invention will be better understood by reference to the following examples:

| Example Number | Percentage by Weight | Component |
|---|---|---|
| 1 | 31.8 | Glycerin |
|   | 0.2 | Quaternium-15[1] |
|   | 21 | Propylene Glycol |
|   | 1 | Hydrocortisone |
|   | 25 | Karaya |
|   | 21 | HB Fuller 3120z[2] |
| 2 | 31.8 | Glycerin |
|   | 0.2 | Quaternium-15[1] |
|   | 21.5 | Propylene Glycol |
|   | 0.5 | Hydrocortisone |
|   | 25 | Karaya |
|   | 21 | BF Goodrich 26171[3] |
| 3 | 27.72 | Glycerin |
|   | 0.64 | Quaternium-15[1] |
|   | 24.5 | Propylene Glycol |
|   | 0.5 | Hydrocortisone |
|   | 24.64 | Karaya |
|   | 21 | BF Goodrich 26222[3] |
| 4 | 27.72 | Glycerin |
|   | 0.64 | Quaternium-15[1] |
|   | 24.64 | Propylene Glycol |
|   | 1 | Hydrocortisone |
|   | 25 | karaya |
|   | 21 | BF Goodrich 26171[3] |
| 5 | 33 | Glycerin |
|   | 18 | Karaya |
|   | 9 | 34x[4] |
|   | 0.5 | Hydrocortisone |
|   | 21.5 | Propylene Glycol |
|   | 18 | BF Goodrich 26171[3] |
| 6 | 14 | Methyl Salicylate |
|   | 4 | Camphor |
|   | 6 | Menthol |
|   | 76 | BF Goodrich 26222[3] |
| 7 | 29 | Glycerin |
|   | 16 | Polytec 31x[5] |
|   | 30 | Propylene Glycol |
|   | 1 | Hydrocortisone |

-continued

EXAMPLES

| Example Number | Percentage by Weight | Component |
|---|---|---|
| | 12 | Lodex[6] |
| | 4 | H2O (deionized) |
| | 8 | HB Fuller 3120z[2] |
| 8 | 30.8 | Glycerin |
| | 15.4 | Polytec 31x[5] |
| | 22.8 | Propylene Glycol |
| | 8 | Lidocaine |
| | 12 | Lodex[6] |
| | 3 | H2O (deionized) |
| | 8 | HB Fuller 3120z[2] |
| 9 | 30.8 | Glycerin |
| | 12 | karaya |
| | 6.4 | Lodex[6] |
| | 8 | 34x[4] |
| | 29.8 | Propylene Glycol |
| | 1 | Capsicum |
| | 12 | Flexcryl 1615[7] |
| 10 | 30.8 | Glycerin |
| | 12 | Karaya |
| | 5.4 | Lodex[6] |
| | 9 | 34x[4] |
| | 25.8 | Propylene Glycol |
| | 12 | HB Fuller 3120z[2] |
| | 5 | Benzocaine |
| 11 | 31.4 | Glycerin |
| | 12.6 | Karaya |
| | 5.2 | Lodex[6] |
| | 8 | 34x[4] |
| | 29.8 | Propylene Glycol |
| | 1 | Hydrocortisone |
| | 12 | HB Fuller 3120z[2] |
| 12 | 14 | Methyl Salicylate |
| | 4 | Camphor |
| | 6 | Menthol |
| | 38 | BF Goodrich 26171[3] |
| | 38 | BF Goodrich 26415[3] |
| 13 | 14 | Methyl Salicylate |
| | 4 | Camphor |
| | 6 | Menthol |
| | 45 | BF Goodrich 26415[3] |
| | 31 | BF Goodrich 26222[3] |
| 14 | 17.4 | methyl Salicylate |
| | 7.5 | Camphor |
| | 5.1 | Menthol |
| | 70 | BF Goodrich 26415[3] |
| 15 | 15.6 | Methyl Salicylate |
| | 6.8 | Camphor |
| | 4.6 | Menthol |
| | 25 | BF Goodrich 26171[3] |
| 16 | 19.8 | Karaya |
| | 36.6 | Glycerin |
| | 15.8 | Methyl Salicylate |
| | 2 | Spearmint Oil |
| | 25.8 | HB Fuller 3120z[2] |
| 17 | 19 | Karaya |
| | 37 | Glycerin |
| | 16 | Methyl Salicylate |
| | 2 | Spearmint Oil |
| | 13 | BF Goodrich 26171[3] |
| | 13 | BF Goodrich 26415[3] |
| 18 | 20 | Karaya |
| | 37 | Glycerin |
| | 8 | Methyl Salicylate |
| | 8 | Trolamine Salicylate |
| | 2 | Spearmint Oil |
| | 12.5 | BF Goodrich 26415[3] |
| | 12.5 | BF Goodrich 26222[3] |
| 19 | 15.6 | Methyl Salicylate |
| | 6.8 | Camphor |
| | 4.8 | Menthol |
| | 30 | BF Goodrich 26334[3] |
| | 43 | BF Goodrich 26222[3] |
| 20 | 15 | Trolamine Salicylate |
| | 10 | Menthol |
| | 34 | BF Goodrich 26171[3] |
| | 41 | BF Goodrich 26222[3] |
| 21 | 20.3 | Methyl Salicylate |
| | 6.6 | Menthol |
| | 32.5 | BF Goodrich 26171[3] |
| | 40.6 | BF Goodrich 26222[3] |
| 22 | 15 | Methyl Salicylate |
| | 10 | Menthol |
| | 29 | BF Goodrich 26171[3] |
| | 46 | BF Goodrich 26222[3] |
| 23 | 23 | Karaya |
| | 34 | Glycerin |
| | 11.5 | Methyl Salicylate |
| | 3 | Menthol |
| | 3 | Camphor |
| | 1.5 | Spearmint Oil |
| | 23 | Avery AE259[8] |
| 24 | 22.5 | karaya |
| | 36 | Glycerin |
| | 16 | Methyl Salicylate |
| | 3 | Spearmint Oil |
| | 8 | BF Goodrich 26222[3] |
| | 14.5 | BF Goodrich 26171[3] |
| 25 | 22.5 | Karaya |
| | 35.9 | Glycerin |
| | 11.8 | Methyl Salicylate |
| | 3.1 | Camphor |
| | 3.1 | Menthol |
| | 1.6 | Spearmint Oil |
| | 22 | BF Goodrich 26415[3] |
| 26 | 24 | Karaya |
| | 34 | Glycerin |
| | 15 | Methyl Salicylate |
| | 2 | Spearmint Oil |
| | 12.5 | BF Goodrich 26171[3] |
| | 12.5 | BF Goodrich 26334[3] |
| 27 | 21 | Karaya |
| | 38 | Glycerin |
| | 15 | Methyl Salicylate |
| | 2 | Spearmint Oil |
| | 12 | BF Goodrich 26415[5] |
| | 12 | BF Goodrich 26334[3] |
| 28 | 23 | Karaya |
| | 37.5 | Glycerin |
| | 13.8 | Methyl Salicylate |
| | 1.7 | Spearmint Oil |
| | 12 | BF Goodrich 26171[3] |
| | 12 | Aroset 1196[6] |
| 29 | 22 | Karaya |
| | 36 | Glycerin |
| | 14.2 | Methyl Salicylate |
| | 1.8 | Spearmint Oil |
| | 3 | Camphor |
| | 11.5 | Aroset 1196[9] |
| | 11.5 | BF Goodrich 26222[3] |
| 30 | 22 | Karaya |
| | 35 | Glycerin |
| | 12 | Methyl Salicylate |
| | 3.2 | Menthol |
| | 3.2 | Camphor |
| | 1.6 | Spearmint Oil |
| | 11 | Avery AE259[8] |
| | 12 | BF Goodrich 26171[3] |
| 31 | 54 | Glycerin |
| | 26 | Karaya |
| | 10 | Flexcryl 1615[7] |
| | 3.3 | Eucalyptus Oil |
| | 6.7 | Menthol |
| 32 | 23.5 | Karaya |
| | 33.5 | Glycerin |
| | 15.7 | Methyl Salicylate |
| | 2.8 | Spearmint Oil |
| | 9.1 | BF Goodrich 26222[3] |
| | 15.4 | BF Goodrich 26171[3] |
| 33 | 22.6 | Karaya |
| | 35.9 | Glycerin |

EXAMPLES

| Example Number | Percentage by Weight | Component |
|---|---|---|
|  | 6 | Methyl Salicylate |
|  | 5.9 | Trolamine Salicylate |
|  | 3.2 | Camphor |
|  | 3.2 | Menthol |
|  | 1.5 | Spearmint Oil |
|  | 7.5 | BF Goodrich 26222[3] |
|  | 14.2 | BF Goodrich 26171[3] |
| 34 | 22 | Karaya |
|  | 35 | Glycerin |
|  | 16 | Methyl Salicylate |
|  | 4 | Menthol |
|  | 6 | Camphor |
|  | 2 | Spearmint Oil |
|  | 9 | BF Goodrich 26415[3] |
|  | 6 | BF Goodrich 26171[3] |
| 35 | 20 | Karaya |
|  | 33.8 | Glycerin |
|  | 0.2 | Quaternium-15[1] |
|  | 16 | Methyl Salicylate |
|  | 4 | Menthol |
|  | 6 | Camphor |
|  | 1.5 | Spearmint Oil |
|  | 12 | BF Goodrich 26222[3] |
|  | 6.5 | BF Goodrich 26171[3] |
| 36 | 54 | Glycerin |
|  | 26 | Karaya |
|  | 5 | BF Goodrich 26222[3] |
|  | 5 | BF Goodrich 26171[3] |
|  | 6.7 | Menthol |
|  | 3.3 | Eucalyptus Oil |
| 37 | 53 | Glycerin |
|  | 25 | Karaya |
|  | 9.5 | Flexcryl 1615[7] |
|  | 8.4 | Menthol |
|  | 4.1 | Eucalyptus Oil |
| 38 | 46.5 | Glycerin |
|  | 8.4 | Menthol |
|  | 4.1 | Eucalyptus Oil |
|  | 26 | Karaya |
|  | 15 | Flexcryl 1615[7] |
| 39 | 16.8 | Menthol |
|  | 8.2 | Eucalyptus Oil |
|  | 25 | Avery AE259[8] |
|  | 34 | Glycerin |
|  | 16 | Karaya |
| 40 | 54 | Glycerin |
|  | 26 | Karaya |
|  | 10 | BF Goodrich 26222[3] |
|  | 6.7 | Menthol |
|  | 3.3 | Eucalyptus Oil |
| 41 | 54 | Glycerin |
|  | 26 | Karaya |
|  | 10 | BF Goodrich 26171[3] |
|  | 6.7 | Menthol |
|  | 3.3 | Eucalyptus Oil |
| 42 | 54 | Glycerin |
|  | 31 | Karaya |
|  | 5 | Flexcryl 1615[7] |
|  | 6.7 | Menthol |
|  | 3.3 | Eucalyptus Oil |
| 43 | 54 | Glycerin |
|  | 36 | Karaya |
|  | 6.7 | Menthol |
|  | 3.3 | Eucalyptus Oil |
| 44 | 49 | Glycerin |
|  | 26 | Karaya |
|  | 15 | BF Goodrich 26171[3] |
|  | 6.7 | Menthol |
|  | 3.3 | Eucalyptus Oil |
| 45 | 48 | Glycerin |
|  | 24.5 | Karaya |
|  | 15 | BF Goodrich 26171[3] |
|  | 8.4 | Menthol |
|  | 4.1 | Eucalyptus Oil |
| 46 | 49.3 | Glycerin |
|  | 23.2 | Karaya |
|  | 15 | BF Goodrich 26334[3] |
|  | 8.4 | Menthol |
|  | 4.1 | Salicylic Acid |
| 47 | 50 | Glycerin |
|  | 25 | Karaya |
|  | 15 | BF Goodrich 26171[3] |
|  | 6.7 | Menthol |
|  | 3.3 | Eucalpytus Oil |
| 48 | 47 | Glycerin |
|  | 20.5 | Karaya |
|  | 15 | BF Goodrich 26415[3] |
|  | 11.7 | Menthol |
|  | 5.8 | Eucalyptus Oil |
| 49 | 49.3 | Glycerin |
|  | 23.2 | Karaya |
|  | 15 | BF Goodrich 26171[3] |
|  | 8.4 | Menthol |
|  | 4.1 | Eucalyptus Oil |
| 50 | 47 | Glycerin |
|  | 24.8 | Karaya |
|  | 6.7 | Menthol |
|  | 3.3 | Eucalyptus Oil |
|  | 18.2 | Aroset 1196[9] |

Footnotes:
[1]Quaternium-15 is a preservative comprising azoniaadamantane chloride by Dow Chemical of Palatine, IL.
[2]HB Fuller 3120z is a residual vinyl acetate monomer resin emulsion in water by HB Fuller of Vadnais Heights, MN.
[3]BF Goodrich 26171, 26222, 26334 and 26415 are acrylic ester copolymers of anionic emulsion adhesives by BF Goodrich of Brecksville, OH.
[4]34x is an anionic polyacrylamide by Tecna Corporation of Belleville, NJ.
[5]Polytec 31x is a non-ionic polyacrylamide by Tecna Corporation of Belleville, NJ.
[6]Lodex is a carbohydrate comprising Malto Dextrin by American Maize-Product Company of Hammond, IN.
[7]Flexcryl 1615 is an adhesive of vinyl acetate/dioctylmaleate copolymer by Air Products and Chemical Inc of Allentown, PA.
[8]Avery AE269 is an acrylic polymer latex adhesive by Avery Chemical of Mill Hill, PA.
[9]Aroset 1196 is an acrylic polymer adhesive by Ashland Chemical of Columbus, OH.

Many variations of the present invention within the scope of the appended claims will be apparent to those skilled in the art once the principles described herein are understood.

What is claimed is:

1. A non-occlusive medication-containing analgesic adhesive patch for the transdermal delivery of medication into the body of a patient through the skin for the relief of pain including arthritis, backache, and muscular aches and strains comprising, a flexible pressure-sensitive adhesive hydrocolloidal gel matrix as a layer including:
1) a natural or synthetic polymer,
2) a biomedically active pain relieving substance dispersed in the gel matrix layer for being absorbed through the skin into the body of the patient, a flexible backing sheet for supporting the matrix, said backing sheet comprising a sheet of water insoluble material having an upper surface and a lower surface, said patch including both the backing and the matrix layer is non-occlusive with a moisture vapor transmission rate that is greater than that of a person's skin, said adhesive matrix layer is cured so as to solidify in contact with the backing, said adhesive patch having the following portions proceeding from a lower surface of the adhesive patch to said upper surface of the backing:

a) a portion of said pressure-sensitive adhesive matrix layer located below the lower surface of the backing, said layer having an exposed pressure-sensitive adhesive surface for bonding the patch to the skin of the patient, b) an upper portion of the matrix bonded to the backing, c) the backing having a portion that is free of said matrix, d) the backing has an upper surface that is spaced apart from the matrix and said biomedically active substance is dispersed in the matrix such that the matrix releases the biomedically active substance into the body of the patient through said adhesive surface of the matrix that is bonded to the patient's skin.

2. The medication-containing adhesive patch of claim 1 wherein the polymer comprises a member selected from the group consisting of gum karaya, gum acacia, locust bean gum, guar gum, modified guar gum, maltodextrin, carboxymethylcellulose, carboxypropylcellulose, polyacrylamide, polyacrylic acid, vinyl acetate resin, acrylic ester copolymer, carbohydrate, vinyl acetate/dioctyl maleate copolymer, and acrylic polymer.

3. The adhesive patch of claim 1 wherein the biomedically active substance comprises a member selected from the group consisting of trolamine salicylate, methyl salicylate, menthol, camphor, eucalyptus oil, spearmint oil, hydrocortisone, benzocaine, lidocaine, ibuprofen, salicylic acid, capsicum.

4. The adhesive patch of claim 1 wherein the matrix includes a liquid humectant and the natural or synthetic polymer comprises a water soluble or water dispersible hydrocolloid.

5. A non-occlusive medication-containing analgesic adhesive patch for the transdermal delivery of medication into the body of a patient through the skin for the relief of pain including arthritis, backache, and muscular aches and pains comprising, a flexible pressure-sensitive adhesive matrix having a tacky pressure-sensitive surface for bonding the adhesive patch to the skin of the patient and said matrix includes:

1) a natural or synthetic water soluble or water dispersible polymer, 2) a biomedically active pain relieving substance dispersed in the adhesive matrix for being absorbed through the skin into the body of the patient comprising, a member selected from the group consisting of trolamine salicylate, methyl salicylate, menthol, camphor, eucalyptus oil, spearmint oil, hydrocortisone, benzocaine, lidocaine, ibuprofen, salicylic acid, capsicum, a flexible backing sheet for supporting the matrix, said backing sheet comprising a sheet of water insoluble material having an upper surface and a lower surface, said patch including both the backing and the matrix layer is non-occlusive with a moisture vapor transmission rate of at least about 612 g/m$^2$/24 hr, said adhesive matrix layer is cured so as to solidify in contact with the backing, said adhesive patch having the following portions proceeding from a lower surface of the adhesive patch to said upper surface of the backing:

a) a layer of said matrix located below the lower surface of the backing, said layer having an exposed adhesive surface for bonding the patch to the skin of the patient, b) an upper portion of the matrix bonded to the backing, c) the backing having a portion that is free of said matrix, d) the backing has an upper surface that is spaced apart from the matrix, and said biomedically active substance is dispersed in the matrix such that the matrix releases the biomedically active substance into the body of the patient through said adhesive surface of the matrix that is bonded to the patient's skin.

6. The adhesive patch of claim 5 wherein the flexible pressure-sensitive adhesive matrix comprises a member selected from the group consisting of gum karaya, gum acacia, locust bean gum, guar gum, modified guar gum, maltodextrin, carboxymethylcellulose, carboxypropylcellulose, polyacrylamide, polyacrylic acid, vinyl acetate resin, acrylic ester copolymer, carbohydrate, vinyl acetate/dioctyl maleate copolymer, and acrylic polymer.

7. The adhesive patch of claim 5 wherein the pressure-sensitive adhesive matrix comprises a resin emulsion adhesive.

8. The adhesive patch of claim 7 wherein the resin emulsion adhesive comprises a member selected from the group consisting of a vinyl acetate resin, acrylic ester copolymer, vinyl acetate/dioctyl maleate copolymer, and acrylic polymer.

9. The adhesive patch of claim 5 wherein the natural or synthetic polymer comprises a water soluble or water dispersible hydrocolloid and the matrix includes a liquid humectant.

10. The adhesive patch of claim 9 wherein the humectant comprises a polyhydric alcohol.

11. The adhesive patch of claim 5 wherein the flexible backing sheet has a release coating applied to a back surface thereof.

12. A non-occlusive medication-containing analgesic adhesive patch for the transdermal delivery of medication into the body of a patient through the skin for the relief of pain including arthritis, backache, and muscular aches and pains comprising, a flexible pressure-sensitive adhesive hydrocolloidal gel matrix including:

1) a natural or synthetic polymer, 2) said polymer comprises a natural or synthetic hydrocolloidal polysaccharide, 3) a biomedically active pain relieving substance dispersed in the matrix for being absorbed through the skin into the body of the patient, 4) the biomedically active substance comprises a member selected from the group consisting of trolamine salicylate, methyl salicylate, menthol, camphor, eucalyptus oil, spearmint oil, hydrocortisone, benzocaine, lidocaine, ibuprofen, salicylic acid, capsicum, 5) a humectant comprising a polyhydric alcohol dispersed in said matrix, 6) a hydrophilic resin emulsion adhesive dispersed in the matrix for enhancing the adhesive qualities of the matrix, a flexible backing sheet for supporting the matrix, said backing sheet comprising a sheet of water insoluble material having an upper surface and a lower surface, said patch including both the backing and the matrix layer is non-occlusive with a moisture vapor transmission rate of at least about 612 g/m$^2$/24 hr, said adhesive matrix layer is cured so as to solidify in contact with the backing, said adhesive patch having the following portions proceeding from a lower surface of the adhesive patch to said upper surface of the backing:
  a) a layer of said matrix located below the lower surface of the backing, said layer having an exposed adhesive surface for bonding the patch to the skin of the patient,
  b) an upper portion of the matrix bonded to the backing,
  c) the backing having a portion that is free of said matrix,
  d) the backing has an upper surface that is spaced apart from the matrix and said biomedically active pain relieving substance is dispersed in the matrix such that the matrix releases the biomedically active substance into the body of the patient through said adhesive surface of the matrix that is bonded to the patient's skin.

13. The adhesive patch of claim 12 wherein the flexible pressure-sensitive adhesive matrix comprises a member selected from the group consisting of gum karaya, gum acacia, locust bean gum, guar gum, modified guar gum, maltodextrin, carboxymethylcellulose, carboxypropylcellulose, polyacrylamide, polyacrylic acid, vinyl acetate resin, acrylic ester copolymer, carbohydrate, vinyl acetate/dioctyl maleate copolymer, and acrylic polymer.

14. The adhesive patch of claim 12 wherein the humectant comprises a polyhydric alcohol selected from the group consisting of glycerol, propylene glycol, ethylene glycol and sorbitol.

* * * * *

REEXAMINATION CERTIFICATE (4565th)
United States Patent
Rolf et al.

(10) Number: US 5,741,510 C1
(45) Certificate Issued: Apr. 30, 2002

(54) ADHESIVE PATCH FOR APPLYING ANALGESIC MEDICATION TO THE SKIN

(75) Inventors: David Rolf, Minneapolis, MN (US); Elisabeth K. Sjoblom Urmann, Tomahawk, WI (US)

(73) Assignee: Lectec Corporation, Minnetonka, MN (US)

Reexamination Request:
No. 90/005,878, Dec. 7, 2000

Reexamination Certificate for:
Patent No.: 5,741,510
Issued: Apr. 21, 1998
Appl. No.: 08/629,191
Filed: Apr. 8, 1996

( * ) Notice: This patent is subject to a terminal disclaimer.

Related U.S. Application Data

(63) Continuation of application No. 08/219,982, filed on Mar. 30, 1994, now Pat. No. 5,536,263.

(51) Int. Cl.⁷ .................. A61F 13/02; A61F 13/00
(52) U.S. Cl. .............. 424/448; 424/449; 604/307
(58) Field of Search .................. 424/448, 449

(56) References Cited

U.S. PATENT DOCUMENTS

| | | | |
|---|---|---|---|
| 4,668,564 A | 5/1987 | Orchard | 428/246 |
| 4,725,439 A | 2/1988 | Campbell et al. | 424/449 |
| 4,803,078 A | 2/1989 | Sakai | 424/445 |
| 4,867,982 A | 9/1989 | Campbell et al. | 424/449 |
| 5,423,737 A | 6/1995 | Cartmell et al. | 602/57 |
| 5,501,661 A | 3/1996 | Cartmell et al. | 602/58 |

*Primary Examiner*—Gollamudi S. Kishore

(57) ABSTRACT

A medication patch to be applied to the skin includes a self-supporting backing layer to give the patch the required integrity and strength by acting as a supporting framework for other components, and a flexible hydrophilic pressure-sensitive adhesive reservoir comprising a natural or synthetic polymer for the sustained release of medication to be absorbed topically through the skin into the body of a patient. The reservoir has two portions: first, an external coating layer with an exposed lower skin-contacting surface that forms a pressure-sensitive bond with the skin, and second, an upper internal portion which infiltrates the porous backing and becomes solidified therein after being applied so that the reservoir and the backing are unified, enabling the backing itself to act as a storage location for the medication containing reservoir. The medication within the reservoir migrates over time from within the backing through the lower coating layer and passes through the skin to provide sustained release of the medication into the body of a patient.

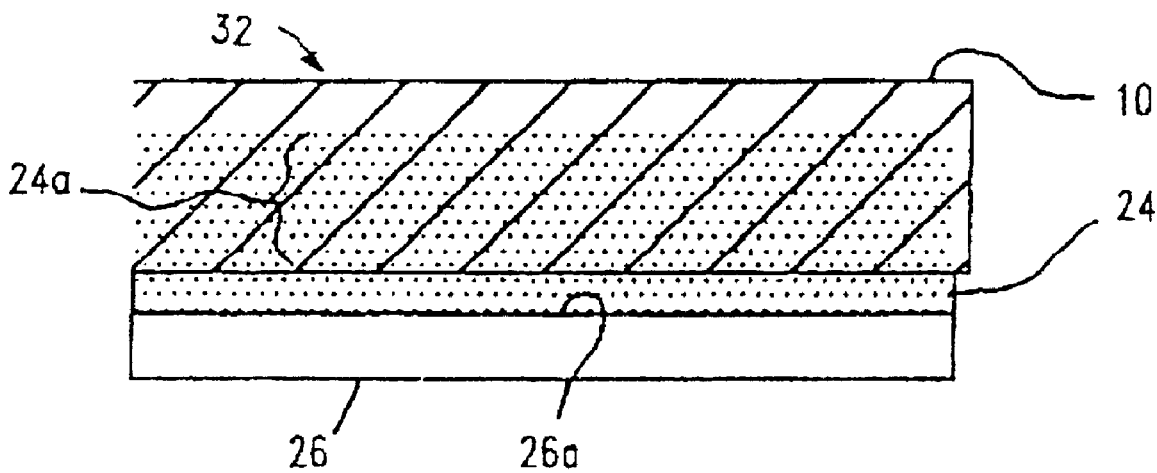

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

\* \* \* \* \*